United States Patent
Nishi

(10) Patent No.: US 11,511,003 B2
(45) Date of Patent: Nov. 29, 2022

(54) IMAGE FORMING APPARATUS THAT CONTROLS A GERMICIDAL LAMP APPARATUS GENERATING GERMICIDAL LIGHT

(71) Applicant: TOSHIBA TEC KABUSHIKI KAISHA, Tokyo (JP)

(72) Inventor: Takayuki Nishi, Fujisawa Kanagawa (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/527,075

(22) Filed: Nov. 15, 2021

(65) Prior Publication Data
US 2022/0296743 A1 Sep. 22, 2022

(30) Foreign Application Priority Data
Mar. 16, 2021 (JP) .............................. JP2021-042971

(51) Int. Cl.
G06F 3/12 (2006.01)
H04N 1/00 (2006.01)
A61L 2/08 (2006.01)

(52) U.S. Cl.
CPC ............ *A61L 2/084* (2013.01); *G06F 3/1204* (2013.01); *G06F 3/1221* (2013.01); *G06F 3/1229* (2013.01); *G06F 3/1255* (2013.01); *H04N 1/0049* (2013.01); *H04N 1/00896* (2013.01); *A61L 2202/11* (2013.01); *A61L 2202/14* (2013.01)

(58) Field of Classification Search
CPC .... G06F 3/1204; G06F 3/1221; G06F 3/1229; G06F 3/1255; H04N 1/0049; H04N 1/00896; A61L 2/084; A61L 2202/11; A61L 2202/14
USPC ......................................................... 358/1.13
See application file for complete search history.

(56) References Cited

U.S. PATENT DOCUMENTS

2017/0246329 A1* 8/2017 Lloyd ...................... A61L 2/084
2020/0197550 A1* 6/2020 Barron .................... A61L 2/084

FOREIGN PATENT DOCUMENTS

| JP | 3012680 U | 6/1995 |
| JP | 2007-068651 A | 3/2007 |
| JP | 2010-164815 A | 7/2010 |
| JP | 2017-029293 A | 2/2017 |
| JP | 2018-007929 A | 1/2018 |

* cited by examiner

*Primary Examiner* — Allen H Nguyen
(74) *Attorney, Agent, or Firm* — Kim & Stewart LLP

(57) ABSTRACT

According to an embodiment, an image forming apparatus supplies, in a normal mode, electric power to an image forming device, and limits, in a power saving mode, power supplying to the image forming device to be less than that in the normal mode. The image forming apparatus communicates, in the normal mode, with a germicidal lamp apparatus via a communication interface such that the germicidal lamp apparatus generates no germicidal light, and communicates, in the power saving mode, with the germicidal lamp apparatus via the communication interface such that the germicidal lamp apparatus generates germicidal light.

10 Claims, 9 Drawing Sheets

IMAGE FORMING APPARATUS THAT CONTROLS A GERMICIDAL LAMP APPARATUS GENERATING GERMICIDAL LIGHT

CROSS-REFERENCE TO RELATED APPLICATIONS

This application is based upon and claims the benefit of priority from the prior Japanese Patent Application No. 2021-042971, filed on Mar. 16, 2021, the entire contents of which are incorporated herein by reference.

FIELD

An embodiment to be described here generally relates to an image forming apparatus and a germicidal lamp apparatus.

BACKGROUND

A convenient stand-type germicidal lamp that can be easily moved and placed in a kitchen of a cafeteria, a guest room of a hotel, or the like is known. This germicidal lamp is turned off when a human body detection sensor detects the entrance of a person into the application range of germicidal light that may affect the human body.

The use of germicidal lamps to sterilize equipment touched by humans has been considered. From the viewpoint of safety, it is desired to reliably control the germicidal lamp such that the germicidal light is applied when the person is not within the application range of the germicidal light, the germicidal light is not applied when the person touches the equipment, and the operation load is not imposed on the person.

DETAILED DESCRIPTION

In accordance with an embodiment, an image forming apparatus controls a germicidal lamp apparatus generating germicidal light. The image forming apparatus includes: an image forming device, a communication interface, and a processor. The communication interface communicates with the germicidal lamp apparatus. The processor causes a power supplying mode for supplying electric power to the image forming device to transition between a normal mode and a power saving mode. The processor supplies, in the normal mode, electric power to the image forming device. The processor limits, in the power saving mode, power supplying to the image forming device to be less than that in the normal mode. The processor communicates, in the normal mode, with the germicidal lamp apparatus via the communication interface to cause the germicidal lamp apparatus to generate no germicidal light. Further, the processor communicates, in the power saving mode, with the germicidal lamp apparatus via the communication interface to cause the germicidal lamp apparatus to generate germicidal light.

Figure 1:
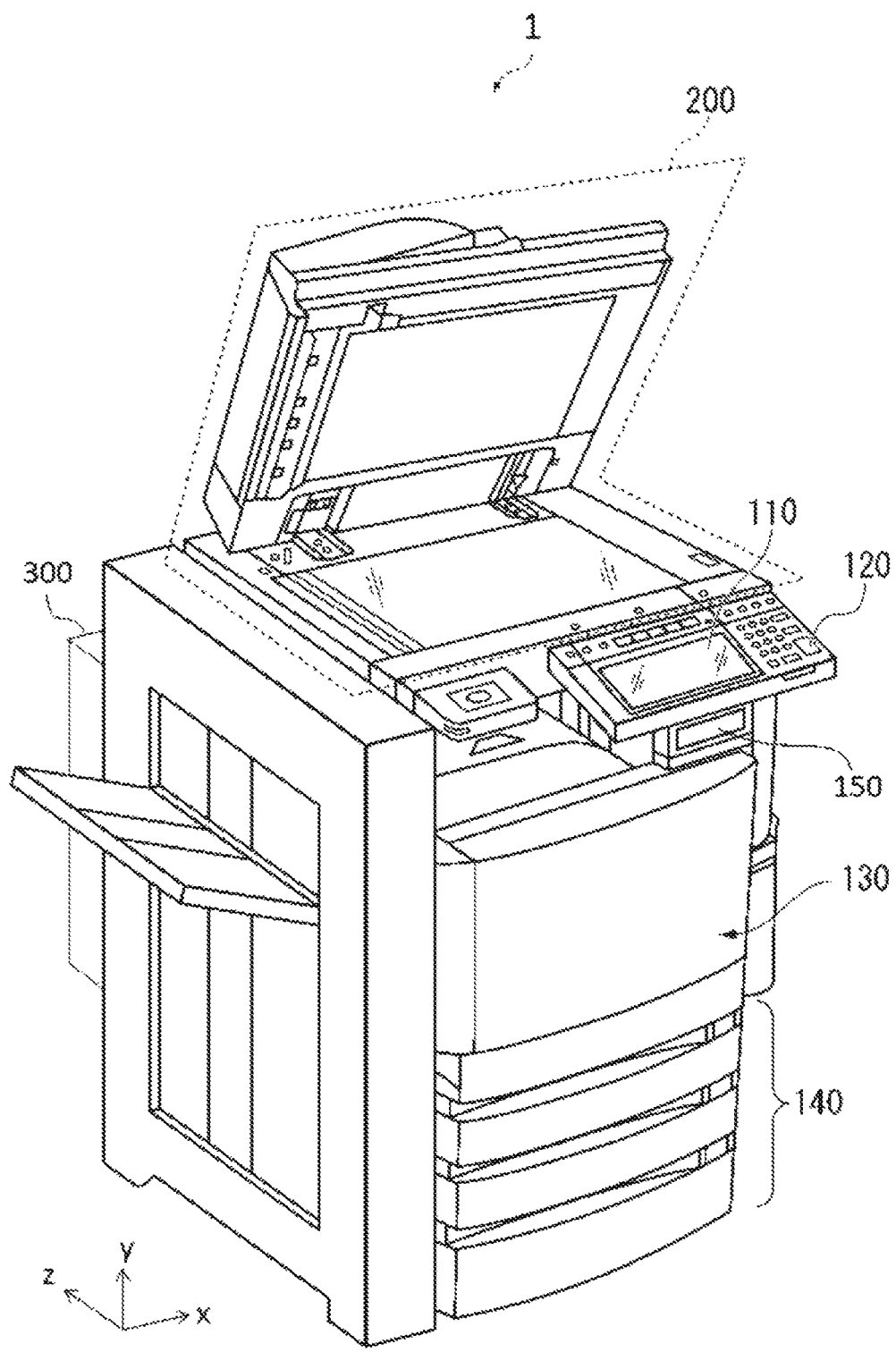
FIG. 1 is a perspective view showing the appearance of an image forming apparatus according to an embodiment as viewed from front upper left.

Hereinafter, an embodiment of an image forming apparatus that reliably controls a germicidal lamp such that the operating load is not imposed on a person will be described with reference to the drawings. FIG. 1 is a perspective view showing the appearance of an image forming apparatus 1 according to an embodiment as viewed from front upper left. An arrow x in FIG. 1 indicates a direction from the left side to the right side of the image forming apparatus 1. An arrow y indicates a direction from the floor side to the up side of the image forming apparatus 1. An arrow z indicates a direction from the front side to the rear side of the image forming apparatus 1.

As shown in FIG. 1, the image forming apparatus 1 includes a display 110, a control panel 120, an image forming device 130, an image reading device 200, a motion detector 150, and a system controller 300.

A toner cartridge is attached to the image forming apparatus 1. The image forming apparatus 1 forms an image on a sheet using a toner deposited in a toner cartridge. The toner cartridge may be filled with a color fadable toner capable of fading a color after an image is formed or a toner that is not capable of fading a color after an image is formed.

The display 110 includes an image display device such as a liquid crystal display and an organic EL (Electro Luminescence) display. The display 110 displays various types of information regarding the image forming apparatus 1.

The control panel 120 includes a plurality of buttons for receiving a user operation. The display 110 and the control panel 120 may be configured as an integral touch panel.

The image forming device 130 forms an image on the sheet on the basis of image information generated by the image reading device 200 or image information received via a communication path.

The image reading device 200 reads image information to be read as light and dark. The image reading device 200 then reads the read image information. The stored image information may be transmitted to another information processing apparatus via a network. The stored image information may be output to the image forming device 130. The image forming device 130 forms an image on the sheet on the basis of the image information described above.

The motion detector 150 detects a person present in the vicinity of the image forming apparatus 1. The motion detector 150 outputs a detection signal in the case where a person is within a detection range. The motion detector 150 may include a sensor that detects light changes caused by movement of a person. The motion detector 150 may include a pyroelectric sensor that detects changes in infrared rays caused by movement of a person. The system controller 300 controls the respective units in order to realize the function as the image forming apparatus 1.

Figure 2:
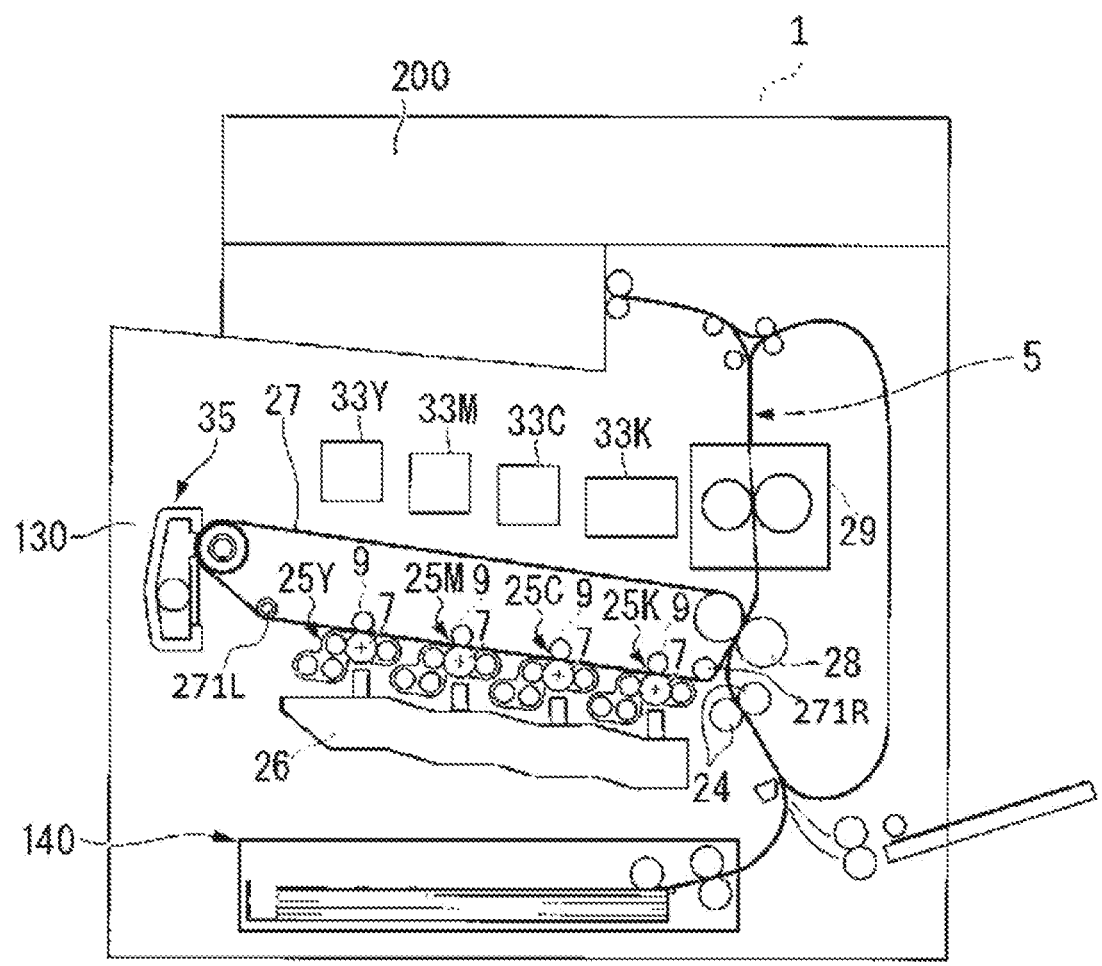
FIG. 2 is a schematic cross-sectional view showing the image forming apparatus according to the embodiment as viewed from the front side.

FIG. 2 is a configuration diagram of the image forming apparatus 1 as viewed from the front side. The image forming apparatus 1 includes the image reading device 200 and the image forming device 130.

The image forming device 130 includes a sheet housing device 140, a transport device 5, an image forming station 25Y, an image forming station 25M, an image forming station 25C, an image forming station 25K, an exposure device 26, a transfer belt 27, a fixing device 29, toner cartridges 33Y, 33M, 33C, and 33K, and a transfer belt cleaner 35.

The sheet housing device 140 houses a sheet. The transport device 5 includes a resist roller 24 and a transfer roller 28. The resist roller 24 adjusts the posture of the distal end of the sheet taken out from the sheet housing device 140 and transports the sheet in accordance with the timing at which the image forming device 130 transfers a toner image to the sheet. The resist roller 24 transports the sheet to the transfer roller 28.

The transfer belt 27 has an image forming surface that is a surface facing the image forming stations 25Y, 25M, 25C, and 25K. The image forming surface is inclined at a predetermined inclination angle with respect to the floor so as to be lower from the left side to the right side when viewed from the front side in order to obtain a sufficient length. Rollers 271L and 271R defining the predetermined inclination angle of the image forming surface are disposed on the back surface of the image forming surface of the transfer belt 27. Further, each of the image forming stations 25Y, 25M, 25C, and 25K faces the transfer belt 27 between the rollers 271L and 271R. Further, transfer rollers 9 are disposed on the back surface of the surface of the transfer belt 27 that each of the image forming stations 25Y, 25M, 25C, and 25K faces between the rollers 271L and 271R. Each of the image forming stations 25Y, 25M, 25C, and 25K includes a photoreceptor drum 7 on which a toner image is to be formed, as described below. The transfer rollers 9 include the transfer rollers 9 for transferring toner images from the respective photoreceptor drums 7 of the image forming stations 25Y, 25M, 25C, and 25K to the transfer belt 27. The transfer belt 27 transports, to the secondary transfer position by the transfer roller 28, the toner images of the respective colors overlappingly transferred in order from the respective photoreceptor drums 7 of the image forming stations 25Y, 25M, 25C, and 25K. The transfer roller 28 transfers the toner image from the transfer belt 27 to the sheet.

The image forming stations 25Y, 25M, 25C, and 25K are disposed in order along the traveling direction of the surface of the transfer belt 27 facing the image forming stations 25Y, 25M, 25C, and 25K. The image forming stations 25Y, 25M, 25C, and 25K are disposed near the floor in order from the left side to the right side when viewed from the front side and along the transfer belt 27 inclined with respect to the floor, i.e., along an inclination angle D. The image forming station 25Y forms an yellow toner image. The image forming station 25M forms a magenta toner image. The image forming station 25C forms a cyan toner image. The image forming station 25K forms a black toner image. Each of the image forming stations 25Y, 25M, 25C, and 25K includes the photoreceptor drum 7, and performs charging, developing, cleaning, discharging, and the like on the photoreceptor drum 7 in order to form a toner image on the photoreceptor drum 7.

The exposure device 26 exposes the four photoreceptor drums 7 to form an electrostatic latent image.

The fixing device 29 fixes the toner image on the sheet to which the toner image has been transferred by the transfer roller 28.

Toner cartridges 33Y, 33M, 33C, and 33K are attached above the transfer belt 27. The toner cartridge 33Y houses a yellow toner for replenishing the image forming station 25Y through a replenishment tube. The toner cartridge 33M houses a magenta toner for replenishing the image forming station 25M through a replenishment tube. The toner cartridge 33C houses a cyan toner for replenishing the image forming station 25C through a replenishment tube. The toner cartridge 33K houses a black toner for replenishing the image forming station 25K through a replenishment tube.

The transfer belt cleaner 35 removes the toner remaining on the transfer belt 27 after the toner image is transferred to the sheet by the transfer roller 28.

Figure 3:
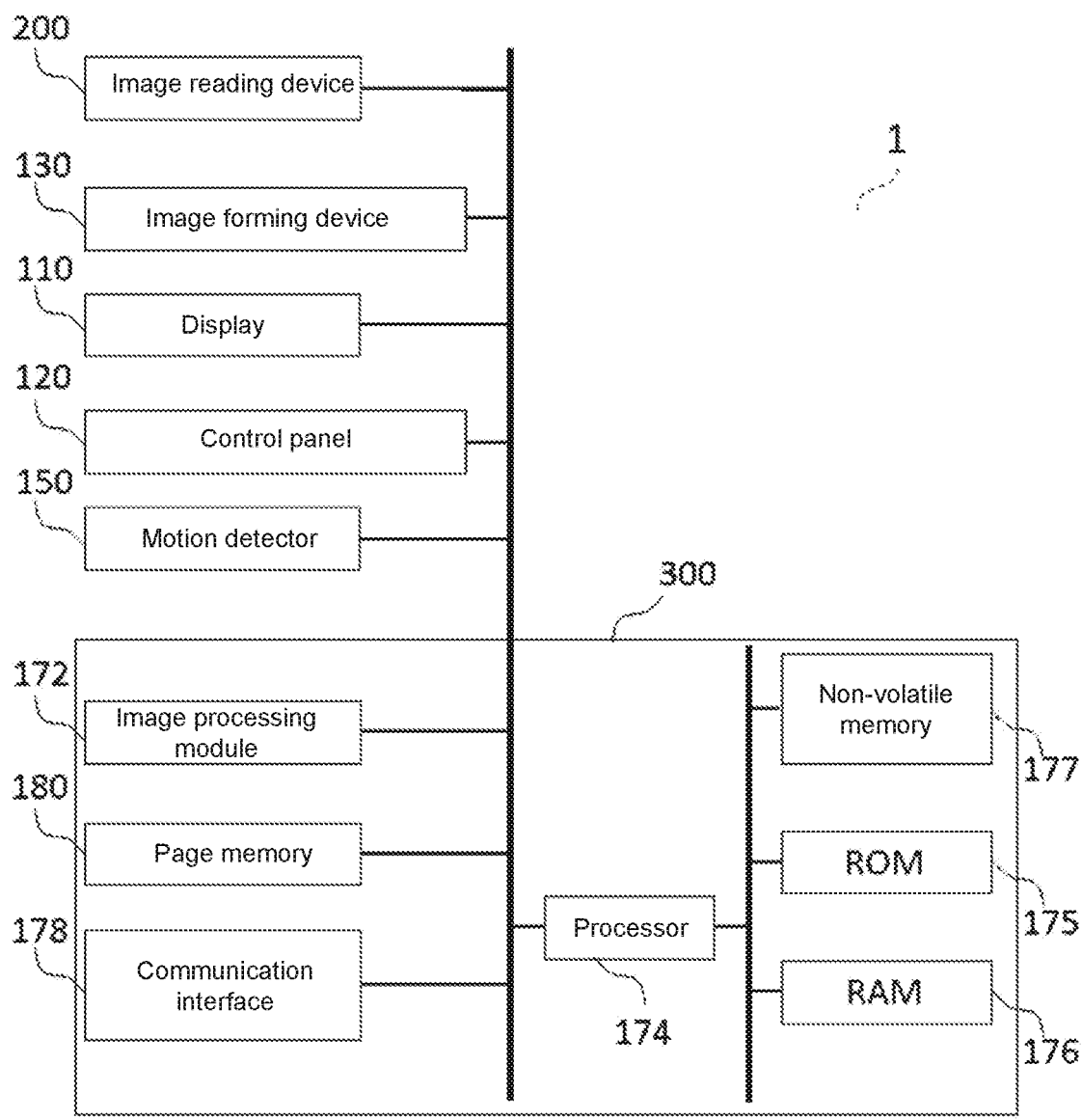
FIG. 3 is a block diagram showing the image forming apparatus according to the embodiment.

FIG. 3 is a block diagram showing the image forming apparatus 1. The image forming apparatus 1 includes the image reading device 200, the image forming device 130, the display 110, the control panel 120, the motion detector 150, and the system controller 300. The system controller 300 includes an image processing module 172, a processor 174, a ROM (Read Only Memory) 175, a RAM (Random Access Memory) 176, a non-volatile memory 177, a communication interface 178, and a page memory 180.

The image reading device 200 outputs an image of an optically read manuscript as image data.

The image processing module 172 performs various types of image processing on the image data acquired by the image reading device 200 or the image data input via the communication interface 178. The page memory 180 stores the image data output by the image processing module 172.

The image forming device 130 forms an image on the basis of the image data stored in the page memory 180.

The communication interface 178 is an interface for communicating with another device. The communication interface 178 is used to communicate with an external device. The communication interface 178 includes, for example, a wired LAN communication adapter. The communication interface 178 may function as PSE (Power sourcing equipment) in so-called PoE (Power over Ethernet) standards such as IEEE 802.3af, IEEE802.3at, and IEEE 802.3bt. The communication interface 178 includes, for example, a USB (universal serial bus) communication adapter. The communication interface 178 may include one performing wireless communication with another device in accordance with a communication standard, such as a wireless LAN communication adapter and a short-range wireless communication adapter.

The display 110 displays various types of information regarding the image forming apparatus 1. The display 110 displays, for example, an image for setting various functions of the image forming apparatus 1 or an image indicating the toner remaining amount.

The control panel 120 receives an input of a user operation.

The processor 174 controls the respective units in order to realize the function as the image forming apparatus 1 in accordance with various programs.

For example, the processor 174 receives a job such as a scan job and a copy job input by a user operating the control panel 120 and stores the job in the RAM 176. The processor 174 receives a print job received from an external device via the communication interface 178 and stores the job in the RAM 176. The processor 174 organizes the scheduling of the jobs stored in the RAM 176, e.g., organizes the execution order by separating the copy job into a scan job and a print job.

The processor 174 controls the image reading operation in the image reading device 200 designated by the scan job. The processor 174 controls the image processing operation in the image processing module 172 designated by the job. The processor 174 controls the image forming operation in the image forming device 130 designated by the print job.

The processor 174 controls, on the basis of the detection signal output by the motion detector 150, power supplying to the image reading device 200, the image forming device 130, the display 110, and the like. The image forming apparatus 1 has, for example, a normal mode and a power saving mode as a mode for power supplying. In the normal mode, electric power is supplied to the image reading device 200, the image forming device 130, the display 110, and the like. In the power saving mode, the power supplying to the image reading device 200, the image forming device 130, the display 110, and the like is limited to be less than that in the normal mode. Also in the power saving mode, electric power is supplied to the motion detector 150.

In the power saving mode, the processor 174 switches the power supplying mode from the power saving mode to the normal mode in the case where a detection signal of the motion detector 150 is received, an operation of the control panel 120 is detected, or a print job is received from an external device via the communication interface 178.

In the normal mode, the processor 174 switches the power supplying mode from the normal mode to the power saving mode in the case where a certain period of time has elapsed while no detection signal of the motion detector 150 is received, no operation of the control panel 120 is detected, and no print job is received from an external device via the communication interface 178.

In the normal mode, the processor 174 postpones switching the power supplying mode to the power saving mode in the case where a detection signal of the motion detector 150 is received, an operation of the control panel 120 is detected, or a print job is received from an external device via the communication interface 178.

In the normal mode, the processor 174 may lengthen and shorten, in the case where the number of pages included in the print job is small and large, respectively, a period of postponing the switching the power supplying mode to the power saving mode in the case where a print job is received from an external device via the communication interface 178.

The processor 174 supplies electric power for power supplying to an external device via the communication interface 178. In the normal mode, the processor 174 stops the power supplying from the communication interface 178 to the external device.

The processor 174 may stop, in the case where a detection signal of the motion detector 150 is received, the power supplying from the communication interface 178 to the external device before starting power supplying to the image reading device 200, the image forming device 130, the display 110, and the like.

The processor 174 may stop, in the case where an operation of the control panel 120 is detected, the power supply from the communication interface 178 to the external device before starting power supplying to the image reading device 200, the image forming device 130, the display 110, and the like.

In the power saving mode, the processor 174 supplies electric power from the communication interface 178 to the external device. The processor 174 may be set to supply electric power from the communication interface 178 to the external device even in the normal mode.

The processor 174 is capable of controlling a period from when the power supplying mode transitions the power saving mode to when electric power is started to be supplied to the external device via the communication interface 178. The processor 174 controls the period from when the power supplying mode transitions the power saving mode to when electric power is started to be supplied to the external device via the communication interface 178 to be a period that can be input by a user operating the control panel 120.

In the normal mode, the processor 174 may lengthen and shorten, in the case where the number of pages included in the print job is small and large, respectively, a period from when the power supplying mode transitions to the power saving mode to when electric power is started to be supplied to an external device via the communication interface 178 in the case where a print job is received from the external device via the communication interface 178.

The processor 174 may transmit, via the communication interface 178, a signal indicating that no detection signal of the motion detector 150 is received or a signal indicating that no operation of the control panel 120 is detected, and supply, to the external device, electric power of an amount necessary for processing the transmitted signal, the amount being less than an amount of power supplying in the power saving mode.

The processor 174 may transmit, via the communication interface 178, a signal indicating the mode of the power supplying, and supply, to the external device, electric power of an amount necessary for processing the transmitted signal, the amount being less than an amount of power supplying in the power saving mode.

The processor 174 may transmit, via the communication interface 178, a signal for controlling an operation of the external device, and supply, to the external device, electric power of an amount necessary for controlling an operation of the external device, the amount being less than an amount of power supplying in the power saving mode. Since the necessary amount described above differs for each external device, the amount of power supplying may be caused to differ for each external device identified by a unique identifier.

In the case where it is difficult to supply electric power to the external device via the communication interface 178, e.g., the power capacity of the image forming apparatus 1 is small, the processor 174 may transmit, via the communication interface 178, a signal indicating that no detection signal of the motion detector 150 is received or a signal indicating that no operation of the control panel 120 is detected, and supply no electric power to the external device.

In the case where it is difficult to supply electric power to the external device via the communication interface 178, e.g., the power capacity of the image forming apparatus 1 is small, the processor 174 may transmit, via the communication interface 178, a signal indicating the mode of the power supplying, and supply no electric power to the external device.

In the case where it is difficult to supply electric power to the external device via the communication interface 178, e.g., the power capacity of the image forming apparatus 1 is small, the processor 174 may transmit, via the communication interface 178, a signal for controlling an operation of the external device, and supply no electric power to the external device. In the case where no electric power is supplied from the image forming apparatus 1 to the external device, the external device needs to be supplied with electric power from other than the image forming apparatus 1.

The processor 174 may receive, via the communication interface 178 from the external device, a signal indicating whether or not a motion detector of the external device has detected a person or the like. The processor 174 may use, as a condition for the transition or continuation of the normal mode and the power saving mode, a signal indicating whether or not a motion detector of the external device has detected a person or the like, similarly to the detection signal of the motion detector 150. In the case where the processor 174 has received, via the communication interface 178 from the external device, a signal indicating whether or not a motion detector of the external device has detected a person or the like, the communication interface 178 may be supplied with electric power even in the power saving mode.

The processor 174 may receive, via the communication interface 178 from the external device, a signal indicating the operation state of the external device. The processor 174 may display, on the basis of the operation state of the external device, the operation state of each external device on the control panel 120.

Such a processor 174 includes, for example, a CPU (Central Processing Unit). The processor 174 includes one or more CPUs. The ROM 175 stores various programs necessary for control by the processor 174, or the like. The RAM 176 temporarily stores data necessary for control by the processor 174. The non-volatile memory 177 stores the updated program, various parameters, and the like. Note that the non-volatile memory 177 may store some or all of the various programs.

Figure 4A:
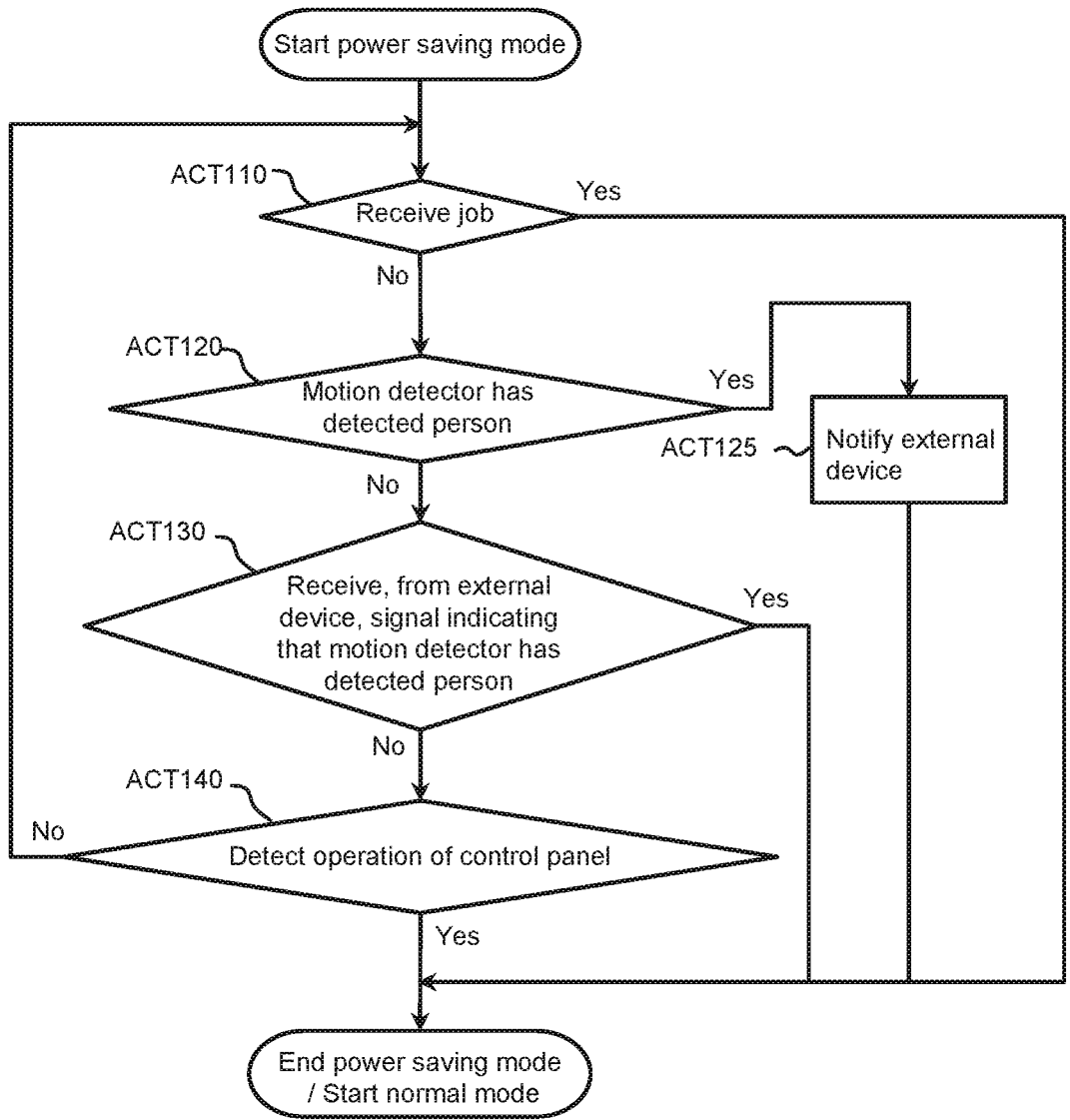
FIG. 4A is a flowchart showing mode control of power supplying of the image forming apparatus according to the embodiment.
Figure 4B:
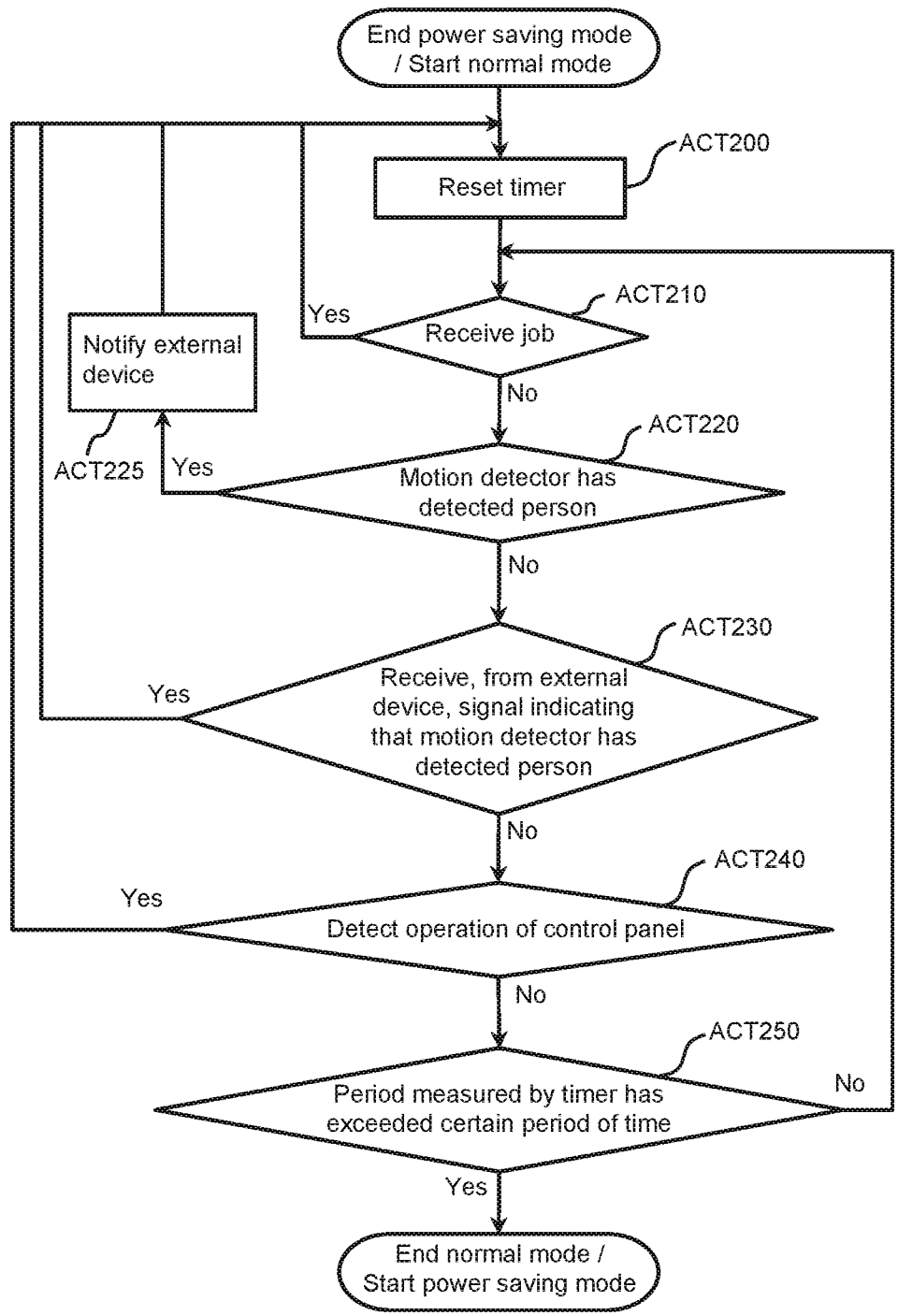
FIG. 4B is a flowchart showing mode control of power supplying of the image forming apparatus according to the embodiment.

FIG. 4A and FIG. 4B show an example of a flowchart showing control by the processor 174 regarding mode control of power supplying.

As shown in FIG. 4A, when the power saving mode is started, in ACT110, the processor 174 checks whether or not the communication interface 178 has received a job from an external device.

In the case where the communication interface 178 has received a job (Yes in ACT110), the processor 174 ends the power saving mode and starts the normal mode.

In the case where the communication interface 178 has not received a job (No in ACT110), the processing of the processor 174 proceeds to ACT120. In ACT120, the processor 174 checks whether or not the motion detector 150 has output a detection signal.

In the case where the motion detector 150 has output a detection signal (Yes in ACT120), the processing of the processor 174 proceeds to ACT125. In ACT125, the processor 174 notifies, via the communication interface 178, an external device of that the motion detector 150 has output a detection signal, and then ends the power saving mode and starts the normal mode.

In the case where the motion detector 150 has not output a detection signal (No in ACT120), the processing of the processor 174 proceeds to ACT130. In ACT130, the processor 174 checks whether or not the communication interface 178 has received, from the external device, a signal indicating that a motion detector of the external device has detected a person or the like.

In the case where a signal indicating that a motion detector of the external device has detected a person or the like is received (Yes in ACT130), the processor 174 ends the power saving mode and starts the normal mode.

In the case where a signal indicating that a motion detector of the external device has detected a person or the like is not received (No in ACT130), the processing of the processor 174 proceeds to ACT140. In ACT140, the processor 174 checks whether or not an input of a user operation has not been made from the control panel 120.

In the case where an input of a user operation has been made from the control panel 120 (Yes in ACT140), the processor 174 ends the power saving mode and starts the normal mode. In the case where an input of a user operation has not been made from the control panel 120 (No in ACT140), the processing of the processor 174 returns to ACT110. The processor 174 performs ACT110 again.

As shown in FIG. 4B, when the normal mode is started, in ACT200, the processor 174 resets a timer. In ACT210, the processor 174 checks whether or not the communication interface 178 has received a job from the external device.

In the case where the communication interface 178 has received a job (Yes in ACT210), the processing of the processor 174 returns to ACT200. The processor 174 performs the processing of ACT200 again. In the case where the communication interface 178 has not receive a job (No in ACT210), the processing of the processor 174 proceeds to ACT220. In ACT220, the processor 174 checks whether or not the motion detector 150 has output a detection signal.

In the case where the motion detector 150 has output a detection signal (Yes in ACT120), the processing of the processor 174 proceeds to ACT225. In ACT225, the processor 174 notifies, via the communication interface 178, the external device of that the motion detector 150 has output a detection signal. After the notification, the processing of the processor 174 returns to ACT200. The processor 174 then performs the processing of ACT200 again. In the case where the motion detector 150 has not output a detection signal (No in ACT220), the processing of the processor 174 proceeds to ACT230. In ACT230, the processor 174 checks whether or not the communication interface 178 has received, from the external device, a signal indicating that a motion detector of the external device has detected a person or the like.

In the case where a signal indicating that a motion detector of the external device has detected a person or the like has been received (Yes in ACT230), the processing of the processor 174 proceeds to ACT200. The processor 174 performs the processing of ACT200 again. In the case where a signal indicating that a motion detector of the external device has detected a person or the like has not been received (No in ACT230), the processing of the processor 174 proceeds to ACT240. In ACT240, the processor 174 checks whether or not an input of a user operation has been made from the control panel 120.

In the case where an input of a user operation has been made from the control panel 120 (Yes in ACT240), the processing of the processor 174 returns to ACT200. The processor 174 performs the processing of ACT200 again. In the case where an input of a user operation has not been made from the control panel 120 (No in ACT240), the processing of the processor 174 proceeds to ACT250. In ACT250, the processor 174 checks whether or not the period measured by the timer has exceeded a certain period of time.

In the case where the period measured by the time has not exceeded a certain period of time (No in ACT250), the processing of the processor 174 returns to ACT210. The processor 174 performs the processing of ACT210 again. In the case where the period measured by the time has exceeded a certain period of time (Yes in ACT250), the processor 174 ends the normal mode and starts the power saving mode.

Figure 5:
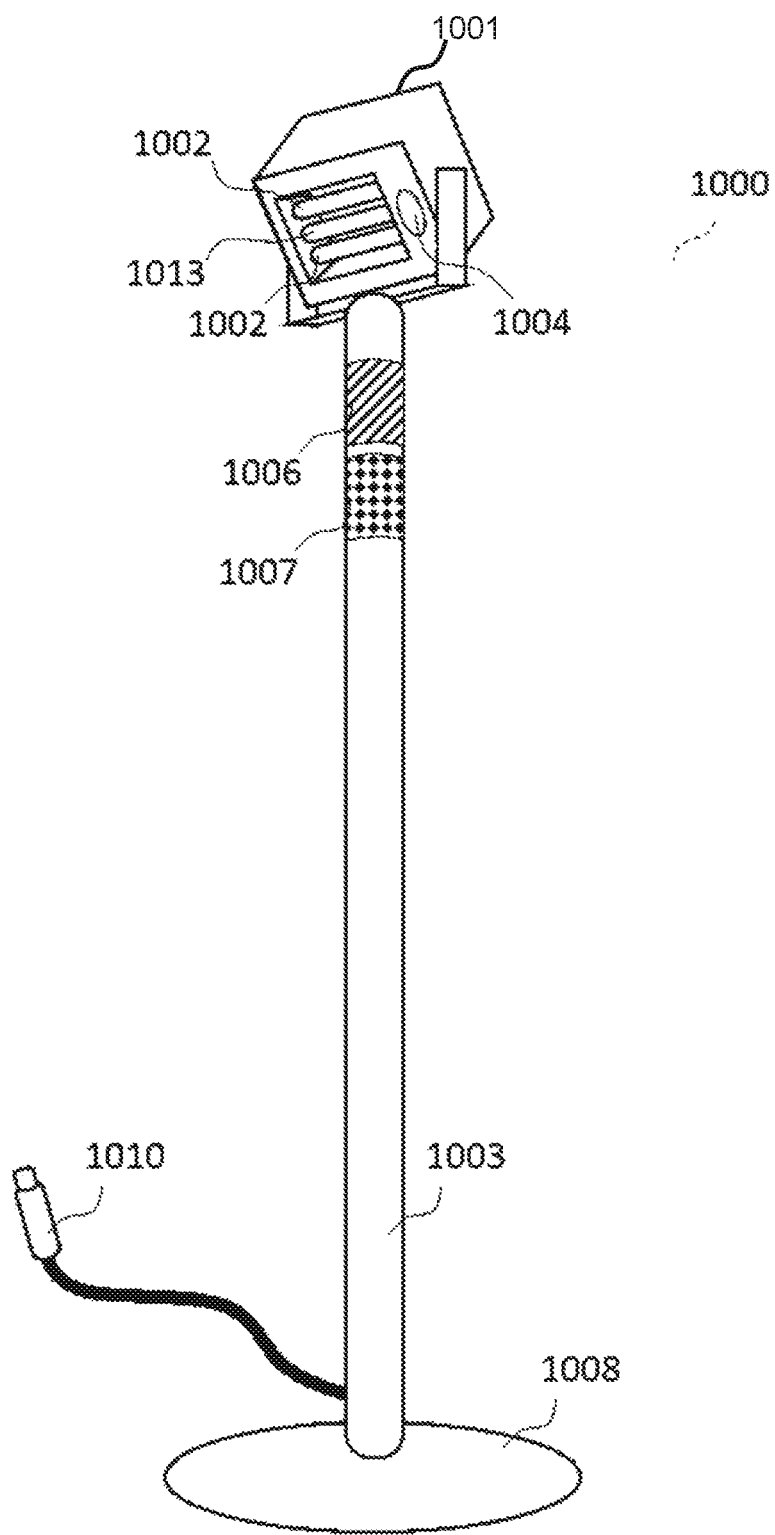
FIG. 5 is a diagram showing the appearance of a germicidal lamp apparatus according to the embodiment.

FIG. 5 is a diagram showing the appearance of a germicidal lamp apparatus 1000 according to an embodiment. The germicidal lamp apparatus 1000 includes a casing 1001, a germicidal lamp 1002, a range notification lamp 1013, a strut 1003, a motion detector 1004, an in-operation display lamp 1006, a pause display lamp 1007, a bottom plate 1008, and a connection terminal 1010.

The casing 1001 supports the germicidal lamp 1002, the range notification lamp 1013, the motion detector 1004, and the like.

The germicidal lamp 1002 generates germicidal light. The germicidal light includes, for example, ultraviolet rays. The germicidal light is reflected by the casing 1001 to be applied downward. The application direction of the germicidal light can be changed by causing the casing 1001 to rotate.

The range notification lamp 1013 generates visible light when the germicidal lamp 1002 generates the germicidal light. The range notification lamp 1013 may include a fluorescent light or an LED (Light Emitting Diode).

The application range of the visible light generated by the range notification lamp 1013 only needs to include the application range of the germicidal light generated by the germicidal lamp 1002. In the case where the germicidal light generated by the germicidal lamp 1002 is invisible or difficult to visually recognize, making the application range of the germicidal light be recognizable by the visible light generated by the range notification lamp 1013 improves the safety for a person.

The motion detector 1004 detects a person present in the vicinity of the germicidal lamp apparatus 1000. The motion detector 1004 outputs a detection signal in the case where a person is present within the detection range.

The motion detector 1004 may include a sensor that detects light changes caused by movement of a person. The motion detector 1004 may include a pyroelectric sensor that detects changes in infrared rays caused by movement of a person. The motion detector 1004 may be one capable of measuring the ambient illuminance or output a high-illuminance detection signal when the detected illuminance is equal to or higher than a predetermined illuminance.

The strut 1003 pivotally supports the casing 1001 in the upward direction. The strut 1003 includes the in-operation display lamp 1006 and the pause display lamp 1007.

The in-operation display lamp 1006 lights when the germicidal lamp 1002 applies the germicidal light. The in-operation display lamp 1006 may include a fluorescent light or an LED. In the case where the germicidal light generated by the germicidal lamp 1002 is invisible or difficult to visually recognize, making the fact that the germicidal lamp 1002 is generating germicidal light be recognizable by the visible light generated by the in-operation display lamp 1006 improves the safety for a person.

The pause display lamp 1007 lights when the germicidal lamp 1002 applies no germicidal light. The pause display lamp 1007 may include a fluorescent light or an LED. In the case where the germicidal light generated by the germicidal lamp 1002 is invisible or difficult to visually recognize, making the fact that the germicidal lamp 1002 is generating germicidal light be recognizable by the visible light generated by the pause display lamp 1007 comforts a person.

The range notification lamp 1013 may be provided on the strut 1003. The motion detector 1004 may be provided on the strut 1003.

The bottom plate 1008 perpendicularly supports from below the strut 1003.

The connection terminal 1010 includes a terminal for communicating with the communication interface 178 of the image forming apparatus 1. The connection terminal 1010 may also serve as a terminal for inputting electric power used in the whole germicidal lamp apparatus 1000. In the case where the germicidal lamp apparatus 1000 is configured to wirelessly communicate with the image forming apparatus 1, the connection terminal 1010 may function only as a terminal for inputting electric power used in the whole germicidal lamp apparatus 1000. Further, in the case where the germicidal lamp apparatus 1000 includes a battery for supplying electric power used in the whole germicidal lamp apparatus 1000, the connection terminal 1010 does not necessarily need to be provided.

Figure 6:
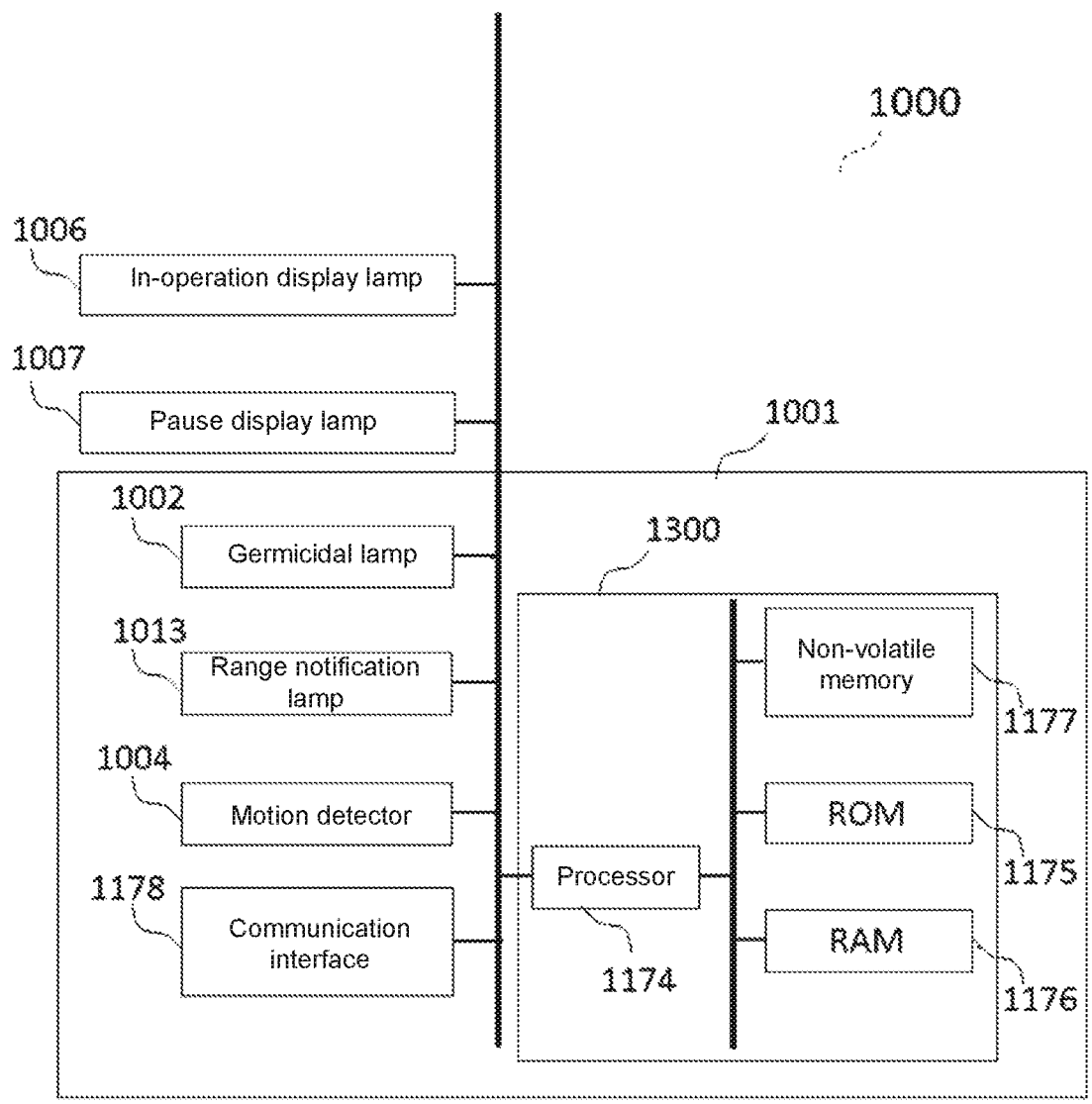
FIG. 6 is a block diagram showing the germicidal lamp apparatus according to the embodiment.

FIG. 6 is a block diagram showing the germicidal lamp apparatus 1000. The germicidal lamp apparatus 1000 includes, in the casing 1001, a system controller 1300 and a communication interface 1178. The system controller 1300 includes a processor 1174, a ROM 1175, a RAM 1176, and a non-volatile memory 1177.

The communication interface 1178 includes an interface for communicating with another device. The communication interface 1178 is used to communicate with an external device. The communication interface 178 includes, for example, a wired LAN communication adaptor. The communication interface 178 may function as a PD (Powered Device) in so-called PoE standards such as IEEE802.3af, IEEE802.3at, and IEEE 802.3bt. The communication interface 178 includes, for example, a USB communication adaptor. The communication interface 1178 may input and output a signal via the connection terminal 1010. The communication interface 1178 functions as a power input circuit in the case where the connection terminal 1010 functions as a terminal for inputting electric power used in the whole germicidal lamp apparatus 1000. The communication interface 1178 may perform wireless communication with another device in accordance with a communication standard, such as a wireless LAN communication adapter and a short-range wireless communication adapter.

The processor 1174 controls, in accordance with various programs, the respective units in order to realize the function as the germicidal lamp apparatus 1000. For example, the processor 1174 causes the range notification lamp 1013 to generate visible light when the germicidal lamp 1002 generates germicidal light. The processor 1174 controls the amount of light emission of the range notification lamp 1013 such that the application range of the visible light generated by the range notification lamp 1013 includes the application range of the germicidal light generated by the germicidal lamp 1002. The processor 1174 causes, in the case where it is detected that the motion detector 1004 has output a detection signal, the germicidal lamp 1002 to stop generating germicidal light. The processor 1174 causes the in-operation display lamp 1006 to light when the germicidal lamp 1002 applies germicidal light. The processor 1174 causes the pause display lamp 1007 to light when the germicidal lamp 1002 applies no germicidal light.

The processor 1174 may cause, in the case where it is detected that the ambient illuminance acquired by the motion detector 1004 is equal to or higher than a predetermined illuminance, the germicidal lamp 1002 to stop generating germicidal light.

The germicidal lamp apparatus 1000 has a germicidal lighting mode and a non-germicidal lighting mode as lighting modes. In the germicidal lighting mode, the processor 1174 causes the range notification lamp 1013 to generate visible light while causing the germicidal lamp 1002 to generate germicidal light. In the non-germicidal lighting mode, the processor 1174 causes the germicidal lamp 1002 to generate no germicidal light and causes the range notification lamp 1013 to generate visible light. In the non-germicidal lighting mode, the processor 1174 may cause the pause display lamp 1007 to light without causing the in-operation display lamp 1006 to light while causing the range notification lamp 1013 to generate visible light.

The processor 1174 receives power supplying from an external device via the communication interface 1178. The processor 1174 causes, in the case where it is not detected that the motion detector 1004 has output a detection signal and power supplying is received from the external device via the communication interface 1178, the germicidal lamp 1002 to generate germicidal light. The processor 1174 causes, in the case where no power supplying is received from the external device via the communication interface 1178, the germicidal lamp 1002 to stop generating germicidal light.

The processor 1174 receives, via the communication interface 1178 from an external device, a signal indicating whether or not a motion detector of the external device has detected a person or the like. The processor 1174 causes, in the case where it is not detected that the motion detector 1004 has output a detection signal and a signal indicating whether or not a motion detector of the external device has not detected a person or the like has been received via the communication interface 1178, the germicidal lamp 1002 to generate germicidal light.

The processor 1174 may make, in the case where a certain period of time has elapsed while it is not detected that the motion detector 1004 has output a detection signal, an inquiry to an external device about whether or not a motion detector of the external device has detected a person or the like, via the communication interface 1178, and cause the germicidal lamp 1002 to generate germicidal light in the case where a signal indicating that the motion detector of the external device has not detected a person or the like has been received as a response. The reason why the external device is inquired about the fact that a person or the like has not been detected is to further avoid the dangerous condition in which a person is present in the application range of germicidal light generated by the germicidal lamp 1002, even if the motion detector 1004 has not detected a person or the like.

The processor 1174 receives, via the communication interface 1178 from the image forming apparatus 1, a signal indicating the mode of the power supplying of the image forming apparatus 1. The processor 1174 causes, in the case where it is detected that the motion detector 1004 has output a detection signal and a signal indicating that the image forming apparatus 1 is in the power saving mode has been received from the image forming apparatus 1 via the communication interface 1178, the germicidal lamp 1002 to generate germicidal light. The processor 1174 causes the germicidal lamp 1002 to stop generating germicidal light when a signal indicating that the image forming apparatus 1 is in the normal mode has been received from the image forming apparatus 1 via the communication interface 1178.

Such a processor 1174 includes, for example, a CPU. The processor 1174 includes one or more CPUs. The ROM 1175 stores various programs necessary for control by the processor 1174, or the like. The RAM 1176 temporarily stores data necessary for control by the processor 1174. The non-volatile memory 1177 stores the updated program, various parameters, and the like. Note that the non-volatile memory 1177 may store some or all of the various programs.

Figure 7:
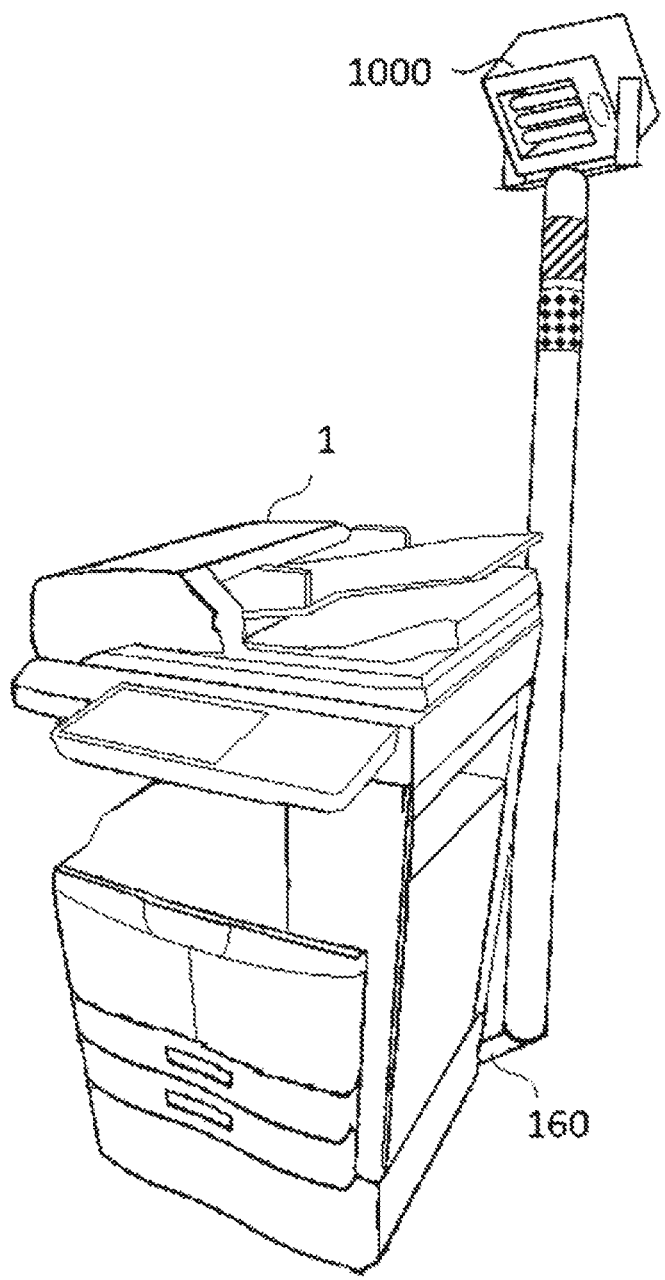
FIG. 7 is a perspective view showing a connection example of the image forming apparatus according to the embodiment and the germicidal lamp apparatus.

FIG. 7 is a perspective view showing a connection example of the image forming apparatus 1 and the germicidal lamp apparatus 1000. The image forming apparatus 1 shown in FIG. 7 includes a connector 160. The germicidal lamp apparatus 1000 is attached to the connector 160 of the image forming apparatus 1, the bottom plate 1008 being not attached to the germicidal lamp apparatus 1000. The connector 160 is rigid enough to support the germicidal lamp apparatus 1000. The connector 160 is connected to the connection terminal 1010 and mediates communication and power suppling between the system controller 300 of the image forming apparatus 1 and the germicidal lamp apparatus 1000. The germicidal lamp apparatus 1000 connected to the image forming apparatus 1 via the connector 160 is suitable for applying germicidal light to a portion that is frequently touched by a person such as the display 110, the control panel 120, and the image reading device 200 of the image forming apparatus 1.

A structure in which the germicidal lamp apparatus 1000 is connected to the image forming apparatus 1 via the connector 160 or the germicidal lamp apparatus 1000 is made stand by itself by the bottom plate 1008 makes it possible to eliminate the necessity for construction work of installation on a ceiling, a wall, a floor, or the like of a building, and facilitate installation. When the in-operation display lamp 1006 and the pause display lamp 1007 of the germicidal lamp apparatus 1000 are provided at positions higher than the image forming apparatus 1, whether or not the germicidal lamp 1002 generates germicidal light can be visually recognized even from a distance, comforting a person.

Figure 8:
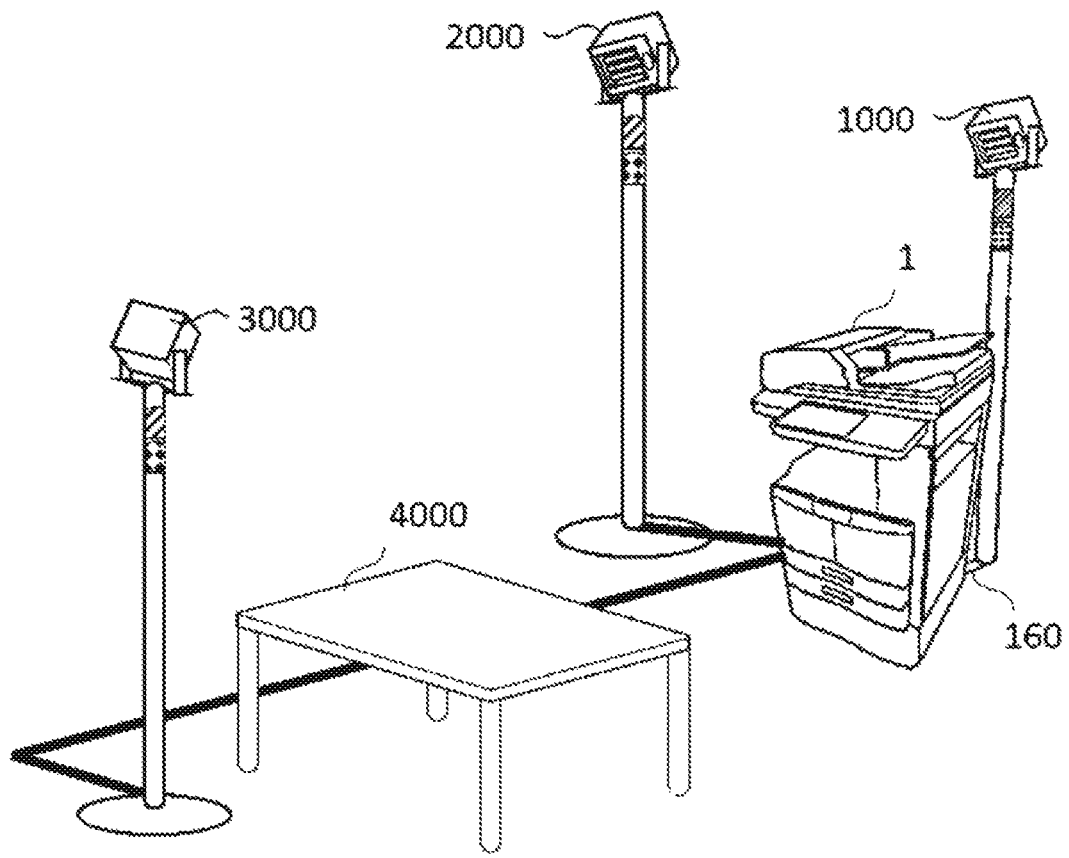
FIG. 8 is a perspective view showing a connection example of the image forming apparatus according to the embodiment and the germicidal lamp apparatus.

FIG. 8 is a perspective view showing a connection example of the image forming apparatus 1 and the germicidal lamp apparatus 1000. The germicidal lamp apparatus 1000 connected to the image forming apparatus 1 via the connector 160 and two germicidal lamp apparatuses 2000 and 3000 to which the bottom plates 1008 are connected communicate with each other. The germicidal lamp apparatus 2000 is disposed at a position where the application range of generated germicidal light does not cover the image forming apparatus 1. The germicidal lamp apparatus 3000 is disposed at a position and a posture where the application range of generated germicidal light covers a desk 4000.

In the case where the image forming apparatus 1 is in the normal mode, each of the germicidal lamp apparatuses 1000, 2000, and 3000 generates no germicidal light. In the case where the image forming apparatus 1 is in the power saving mode, each of the germicidal lamp apparatuses 1000, 2000, and 3000 generates germicidal light.

When the motion detector 150 of the image forming apparatus 1 has detected the presence of a person within the detection range, the system controller 300 of the image forming apparatus 1 may promptly cause each of the germicidal lamp apparatuses 1000, 2000, and 3000 to stop generating germicidal light before the image forming apparatus 1 enters the normal mode from the power saving mode.

When the image forming apparatus 1 has detected an operation of the control panel 120, the system controller 300 of the image forming apparatus 1 may promptly cause each of the germicidal lamp apparatuses 1000, 2000, and 3000 to stop generating germicidal light before the image forming apparatus 1 enters the normal mode from the power saving mode.

For example, as in the germicidal lamp apparatus 3000, the position of the germicidal lamp apparatus is far away from the image forming apparatus 1, i.e., generation of germicidal light does not affect a person operating the image forming apparatus 1 in some cases. In such a case, the germicidal lamp apparatus 3000 may be controlled to generate germicidal light even in the case where the image forming apparatus 1 is in the normal mode.

The system controller 300 of the image forming apparatus may set whether to germicidal light for each of the germicidal lamp apparatuses 1000, 2000, and 3000 that are external devices of the image forming apparatus 1.

For example, as in the germicidal lamp apparatus 3000, in the case where the position of the germicidal lamp apparatus is far away from the image forming apparatus 1, there is a possibility that a person who has finished using the image forming apparatus 1 passes, when he/she leaves, close to the germicidal lamp apparatus 3000. In such a case, even in the case where the image forming apparatus 1 has entered the power saving mode, the germicidal lamp apparatus 3000 may be controlled to generate germicidal light later than when the image forming apparatus 1 has entered the power saving mode. The system controller 300 of the image forming apparatus 1 may set, for each of the germicidal lamp apparatuses 1000, 2000, and 3000 that are external devices of the image forming apparatus 1, how late germicidal light is generated from the time when the image forming apparatus 1 entered the power saving mode, for each unique identifier of the external devices.

Further, in the case where the position of the germicidal lamp apparatus is far away from the image forming apparatus 1 and there is a possibility that a person who has finished using the image forming apparatus 1 passes, when he/she leaves, close to the germicidal lamp apparatus 3000 similarly to the above, the germicidal lamp apparatus 3000 may illuminate a path of the person with visible light even in the case where the image forming apparatus 1 has entered the power saving mode.

The period of postponing the switching the power supplying mode to the power saving mode, the period until power supplying to the germicidal lamp apparatuses 1000, 2000, and 3000 is started, and the period until the germicidal lamp apparatuses 1000,2000, and 3000 are caused to generate germicidal light in the case where the image forming apparatus 1 has received a print job in the normal mode may be lengthened and shortened in the case where the number of pages included in the print job is small and large, respectively. For the sake of safety, the image forming apparatus 1 prevents the germicidal lamp apparatuses 1000, 2000, and 3000 to suddenly generate germicidal light, because it is relatively common for a person to immediately come to pick up a print in the case where the number of pages included in a print job is small.

The system controller 300 of the image forming apparatus 1 may set, in the case where the image forming apparatus 1 has entered the power saving mode, whether to generate visible light from the range notification lamp 1013 for each of the germicidal lamp apparatuses 1000, 2000, and 3000 that are external devices of the image forming apparatus 1, for each unique identifier of the external devices.

The image forming apparatus 1 may display, on the display 110, setting of whether or not germicidal light is generated for each of the germicidal lamp apparatuses 1000, 2000, and 3000 that are external devices of the image forming apparatus 1 and the operation state of whether or not visible light is generated from the range notification lamp 1013.

The system controller 300 of the image forming apparatus 1 may set, in the case where the image forming apparatus 1 has entered the power saving mode, whether to generate visible light from the range notification lamp 1013 for each unique identifier of the external devices.

The system controller 300 of the image forming apparatus 1 may use, as a condition for the transition or continuation of the normal mode and the power saving mode of the image forming apparatus 1, a signal indicating whether or not the motion detector 1004 of each of the germicidal lamp apparatuses 1000, 2000, and 3000 has detected a person or the like, similarly to a detection signal of the motion detector 150 or the detection of an operation of the control panel 120.

The system controller 300 of the image forming apparatus 1 may use, as a condition for the transition or continuation of the normal mode and the power saving mode of the image forming apparatus 1, a signal indicating the operation state of each of the germicidal lamp apparatuses 1000, 2000, and 3000, particularly, whether or not germicidal light is generated.

The system controller 300 of the image forming apparatus 1 may set, for each unique identifier of the external devices, which signal of the germicidal lamp apparatuses 1000, 2000, and 3000 is to be used.

The system controller 300 of the image forming apparatus 1 links the operation state of each of the germicidal lamp apparatuses 1000, 2000, and 3000, particularly, whether or not germicidal light is generated, with the transition or continuation of the normal mode and the power saving mode of the image forming apparatus 1. The system controller 300 of the image forming apparatus 1 is capable of reliably controlling the germicidal lamp apparatuses 1000, 2000, and 3000 such that the operation load is not imposed on a person by considering the operation state of each of the germicidal lamp apparatuses 1000, 2000, and 3000 and whether or not the motion detector 1004 has detected a person or the like as the condition for the transition or continuation of the power supplying mode of the respective units of the image forming apparatus 1.

In the case where each of the germicidal lamp apparatuses 2000 and 3000 is not connected to the image forming apparatus 1 serving as an external device, the germicidal lamp apparatus generates germicidal light when the motion detector 1004 thereof has not detected that a detection signal has been output. In the case where each of the germicidal lamp apparatuses 2000 and 3000 is connected to the image forming apparatus 1 serving as an external device, the germicidal lamp apparatus generates germicidal light when the motion detector 1004 thereof has not detected that a detection signal has been output, the fact that the image forming apparatus 1 serving as an external device has not detected a person or the like can be confirmed, and the fact that the image forming apparatus 1 serving as an external device is in the power saving mode can be confirmed.

In the case where each of the germicidal lamp apparatuses 2000 and 3000 is connected to the image forming apparatus 1 serving as an external device and the positions of the germicidal lamp apparatuses 2000 and 3000 are far away from the image forming apparatus 1, the processor 1174 does not necessarily need to consider, when determining whether or not germicidal light is to be generated, the fact that the image forming apparatus 1 has not detected a person or the like and the image forming apparatus 1 is in the power saving mode.

Whether or not the positions of the germicidal lamp apparatuses 2000 and 3000 are away from the image forming apparatus 1 serving as an external device may be determined on the basis of, for example, whether or not the image forming apparatus 1 is farther than the application range of germicidal light of each of the germicidal lamp apparatuses 2000 and 3000. The distance between the position of each of the germicidal lamp apparatuses 2000 and 3000 and the image forming apparatus 1 serving as an external device may be acquired in accordance with a communication standard such as a wireless LAN communication adapter and a short-range wireless communication adapter.

Note that the germicidal lamp apparatus may include a germicidal lamp that generates germicidal light and a range notification lamp that applies visible light to an application range including the application range of the germicidal light generated by the germicidal lamp. The germicidal lamp apparatus may cause, in the case where the germicidal lamp generates germicidal light, the range notification lamp to generate visible light. The germicidal lamp apparatus may include a motion detector and a processor that stops, in the case where the motion detector has detected a person, causing the germicidal lamp to generate germicidal light. The germicidal lamp apparatus may include an illuminance sensor and a processor that stops, in the case where an ambient illuminance acquired by the illuminance sensor is equal to or higher than a predetermined illuminance, causing the germicidal lamp to generate germicidal light. The germicidal lamp apparatus may include an in-operation display lamp that generates visible light in the case where the germicidal lamp generates germicidal light. The germicidal lamp apparatus may include a pause display lamp that generates visible light in the case where the germicidal lamp generates no germicidal light. The processor of the germicidal lamp apparatus may have a germicidal lighting mode for causing the range notification lamp to generate visible light while causing the germicidal lamp to generate germicidal light and a non-germicidal lighting mode for causing the range notification lamp to generate visible light while causing the germicidal lamp to generate no germicidal light. The processor of the germicidal lamp apparatus may cause, in the non-germicidal lighting mode, the pause display lamp to light without causing the in-operation display lamp to light while causing the range notification lamp to generate visible light. The germicidal lamp apparatus includes a communication interface that communicates with an image forming apparatus. This image forming apparatus supplies, in a normal mode, electric power to an image forming device and limits, in a power saving mode, power supplying to the image forming device to be less than that in the normal mode. The processor of the germicidal lamp apparatus may cause, in the case where the image forming apparatus is in the normal mode, the germicidal lamp to generate no germicidal light and cause, in the case where the image forming apparatus is in the power saving mode, the germicidal lamp to generate germicidal light. The germicidal lamp apparatus includes a communication interface that communicates with an image forming apparatus including a motion detector. The processor of the germicidal lamp apparatus may cause, in the case where a signal indicating that a motion detector of the image forming apparatus has detected a person has been received via the communication interface, the germicidal lamp to generate no germicidal light and cause, in the case where a signal indicating that the motion detector of the image forming apparatus has not detected a person has been received via the communication interface, the germicidal lamp to generate germicidal light. The germicidal lamp apparatus includes a communication interface that communicates with an image forming apparatus including a first motion detector, and a second motion detector. The processor of the germicidal lamp apparatus does not need to cause, in the case where a signal indicating that the first motion detector of the image forming apparatus has detected a person has been received via the communication interface or the second motion detector has detected a person, the germicidal lamp to generate germicidal light. Further, the controller of the germicidal lamp apparatus may cause, in the case where a signal indicating that the first motion detector of the image forming apparatus has not detected a person has been received via the communication interface and the second motion detector has not detected a person, the germicidal lamp to generate germicidal light. The germicidal lamp apparatus includes a communication interface that communicates with an image forming apparatus including a first motion detector, and a second motion detector. The processor of the germicidal lamp apparatus may make, in the case where a certain period of time has elapsed while the second motion detector detects no person via the communication interface, an inquiry to the image forming apparatus, and cause, in the case where a signal indicating that the first motion detector has not detected a person transmitted by the image forming apparatus in response to the inquiry has been received via the communication interface, the germicidal lamp to generate germicidal light.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image forming apparatus that controls a germicidal lamp apparatus generating germicidal light, comprising:
   an image forming device;
   a communication interface that communicates with the germicidal lamp apparatus; and
   a processor configured to
      cause a power supplying mode for supplying electric power to the image forming device to transition between a normal mode and a power saving mode,
      supply, in the normal mode, electric power to the image forming device,
      limit, in the power saving mode, power supplying to the image forming device to be less than that in the normal mode,
      communicate, in the normal mode, with the germicidal lamp apparatus via the communication interface to cause the germicidal lamp apparatus to generate no germicidal light, and
      communicate, in the power saving mode, with the germicidal lamp apparatus via the communication interface to cause the germicidal lamp apparatus to generate germicidal light.

2. The image forming apparatus according to claim 1, further comprising
   a first motion detector that detects whether or not a person is present,
   the processor
      causing, where the first motion detector has detected presence of a person in the power saving mode, the power supplying mode to transition from the power saving mode to the normal mode,
      causing, where the first motion detector has detected non-presence of a person in the normal mode, the power supplying mode to transition from the normal mode to the power saving mode, and
      causing, where a certain period of time has elapsed after the first motion detector detected presence of a person in the normal mode, the power supplying mode to transition from the normal mode to the power saving mode.

3. The image forming apparatus according to claim 2, wherein
the processor communicates, where the first motion detector has detected presence of a person in the normal mode, with the germicidal lamp apparatus via the communication interface such that the germicidal lamp apparatus generates no germicidal light before the power supplying mode transitions to the power saving mode.

4. The image forming apparatus according to claim 1, further comprising
a control panel that receives an input of a user operation,
the processor
causing, where the control panel has received an input of a user operation in the power saving mode, the power supplying mode to transition from the power saving mode to the normal mode,
causing, where the control panel has received no input of a user operation in the normal mode, the power supplying mode to transition from the normal mode to the power saving mode, and
causing, where a certain period of time has elapsed after the control panel received an input of a user operation in the normal mode, the power supplying mode to transition from the normal mode to the power saving mode.

5. The image forming apparatus according to claim 4, wherein
the processor communicates, after the control panel received an input of a user operation in the normal mode, with the germicidal lamp apparatus via the communication interface such that the germicidal lamp apparatus generates no germicidal light before the power supplying mode transitions to the power saving mode.

6. The image forming apparatus according to claim 1, further comprising
a control panel that receives an input of a user operation,
the processor receiving inputting, via the control panel, a period from when the power supplying mode entered the power saving mode to when the germicidal lamp apparatus is caused to generate germicidal light.

7. The image forming apparatus according to claim 1, wherein
the germicidal lamp apparatus includes a second motion detector that detects whether or not a person is present,
the processor
receiving, via the communication interface from the germicidal lamp apparatus, a signal indicating whether or not the second motion detector has detected a person, and
causing, where it is determined that the second motion detector has detected a person on a basis of the signal from the germicidal lamp apparatus, the power supplying mode to transition from the normal mode to the power saving mode.

8. The image forming apparatus according to claim 1, further comprising
a display,
the processor
receiving, via the communication interface from the germicidal lamp apparatus, a signal indicating whether or not the germicidal lamp apparatus generates germicidal light,
displaying, on a basis of the signal from the germicidal lamp apparatus, whether or not the germicidal lamp apparatus generates germicidal light on the display.

9. The image forming apparatus according to claim 1, wherein
the communication interface communicates with an external device to receive a print job from the external device,
the processor
determining, where a print job has been received via the communication interface in the normal mode, the number of print pages on a basis of information included in the print job,
lengthening, where the number of print pages is small, a period until the germicidal lamp apparatus is caused to generate germicidal light, and
shortening, where the number of print pages is large, a period until the germicidal lamp apparatus is caused to generate germicidal light.

10. The image forming apparatus according to claim 2, further comprising
a control panel that receives an input of a user operation,
the processor
checking, where the first motion detector has detected non-presence of a person in the power saving mode, whether or not the control panel has received an input of a user operation, and
causing, where the control panel has received an input of a user operation, the power supplying mode to transition from the power saving mode to the normal mode.

* * * * *